(12) United States Patent
Ku et al.

(10) Patent No.: US 6,599,906 B1
(45) Date of Patent: Jul. 29, 2003

(54) METHOD OF LOCAL ANESTHESIA AND ANALGESIA

(75) Inventors: Baoshan Ku, Beijing (CN); Shiquan Qi, Beijing (CN)

(73) Assignee: Wex Medical Instrumentation Co., Ltd., North Point (HK)

( * ) Notice: Subject to any disclaimer, the term of this patent is extended or adjusted under 35 U.S.C. 154(b) by 0 days.

(21) Appl. No.: 09/702,826

(22) Filed: Nov. 1, 2000

(30) Foreign Application Priority Data

Sep. 18, 2000 (CN) .......................................... 00124518

(51) Int. Cl.⁷ ........................ A61K 31/505; A61K 31/33
(52) U.S. Cl. ........................ 514/257; 514/183; 514/267; 514/272; 514/275; 514/818
(58) Field of Search ................................. 514/183, 257, 514/267, 272, 275, 818

(56) References Cited

U.S. PATENT DOCUMENTS

| | | |
|---|---|---|
| 4,022,899 A | 5/1977 | Adams et al. |
| 4,029,793 A | 6/1977 | Adams et al. |
| 5,846,975 A | 12/1998 | Pan et al. |
| 6,030,974 A | 2/2000 | Schwartz et al. |

FOREIGN PATENT DOCUMENTS

WO   98/51290   * 11/1998

OTHER PUBLICATIONS

C. Y. Kao et al., Pharmacology of Tarichatoxin, vol. 140, 1966, pp. 31–40.
Mari Yotsu et al., Agric. Biol. Chem., vol. 53, No. 3, 1989. pp. 893–895.
Imelda Omana–Zapata et al., Pain, vol. 72, 1997, pp. 41–49. 1997.
Mark S. Wallace, The Clinical Journal of Pain, vol. 16, No. 2, pp. 580–585. 2000.
David J. Bower et al., Clinical Toxicology, vol. 18, No. 7, 1981, pp. 813–863.
C. Y. Kao, Pharmacological Reviews, vol. 13, No. 2, pp. 997–1049. 1966.

* cited by examiner

*Primary Examiner*—Rebecca Cook
(74) *Attorney, Agent, or Firm*—Birch, Stewart, Kolasch & Birch, LLP

(57) ABSTRACT

The present invention provides a method of producing local analgesia and anesthesia in a mammal experiencing pain in a nerve tissue region. The method includes topically administrating to the region, in a suitable pharmaceutical vehicle, an effective dose of a sodium channel blocking compound.

10 Claims, 2 Drawing Sheets

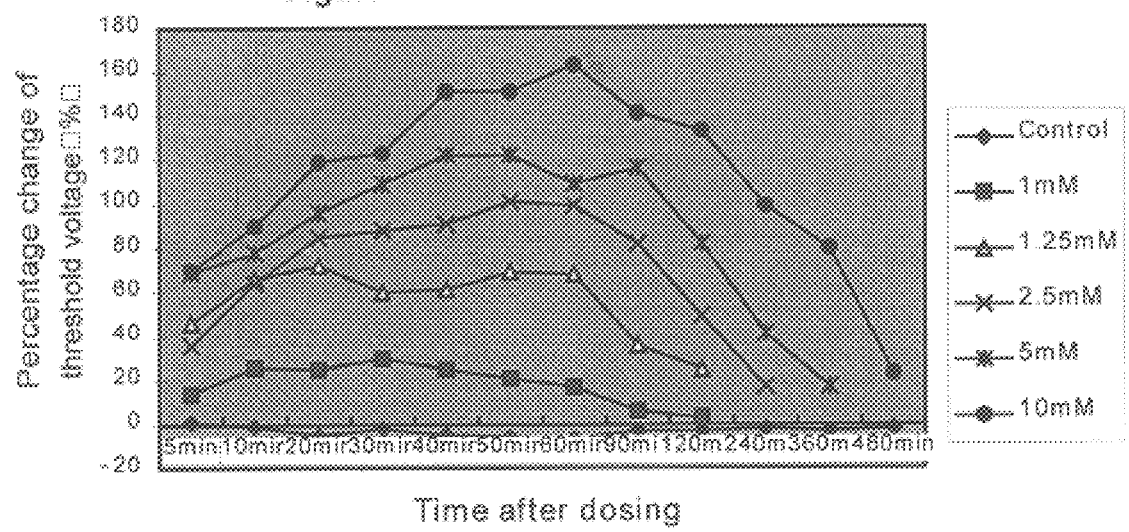

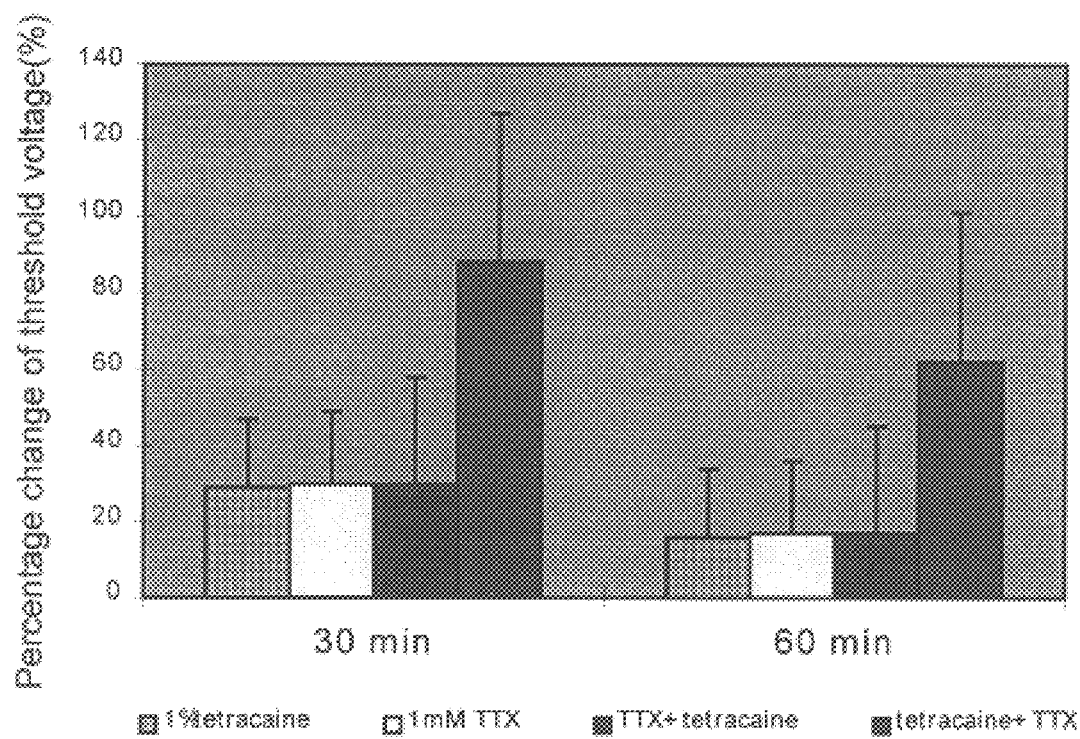

METHOD OF LOCAL ANESTHESIA AND ANALGESIA

FIELD OF THE INVENTION

The present invention relates to a method of producing local anesthesia and analgesia in a nerve tissue region of a mammal by topical administration of sodium channel blocking compounds, including tetrodotoxin and/or saxitoxin.

BACKGROUND OF THE INVENTION

Pain is associated with actual or potential injury or tissue damage due to inflammation, ischemia, mechanical or other irritation. Local anesthetics are used to treat pain by blocking neuronal transmission and affect sensation as well as pain. Analgesics are used to relieve pain and they additionally may interfere with the activity of chemical mediators causing inflammation.

Damage or stimulation to a sensory nerve region such as the dental pulp is usually associated with severe pain and can result from chemical or physical cause, for example, a decayed tooth, periodontitis, and surgical procedures on a tooth.

Pain induced by pulp stimulation is too severe for patients to tolerate. At present, local anesthetics are used to relieve pain, but due to their limited efficacy and short duration of action, they cannot produce a satisfactory effect on patients. For example, procaine and tetracaine are commonly prescribed as topical anesthetics for management of tooth pain. These topical anesthetics provide only partial pain relief for short periods, e.g. about 1 hour.

Therefore, there is a need in the art for methods of producing long lasting, potent anesthesia and analgesia without significant side effects.

Tetrodotoxin can be used as a local anesthetic and is ten thousand times more powerful than commonly used local non-narcotics, as is discussed by C. Y. Kao and F. A. Fulman, J. Pharmacol., 140, 31–40 (1965). Tetrodotoxin preparations in combination with other widely used anesthetics have been noted in U.S. Pat. Nos. 4,022,899 and 4,029,793. According to U.S. Pat. No. 6,030,974, "tetrodotoxin" or "TTX" refers to the amino perhydroquinazoline compounds having the molecular formula $C_{11}H_{17}N_3O_8$ and to derivatives thereof, including but not limited to anhydrotetrodotoxin, tetrodaminotoxin, methoxytetrodotoxin, ethoxytetrodotoxin, deoxytetrodotoxin and tetrodonic acid (Kao). Examples of TTX analogs include novel TTX analogs isolated from various organisms, as well as those that are partially or totally chemically synthesized. See e.g., Yotsu, M. et al. Agric. Biol. Chem., 53(3):893–895 (1989). Such analogs bind to the same site on the alpha subunit of sodium channels as does TTX.

Adams, et al., U.S. Pat. Nos. 4.022,899 and 4,029,793 pertain to a local anesthetic composition comprising a mixture in a pharmaceutically acceptable carrier of a particular toxin, namely tetrodotoxin or desoxytetrodotoxin, and another compound, generally a conventional local anesthetic compound or a similar compound having nerve-blocking properties. The conventional local anesthetic can be an aminoacylanilide such as lidocaine, an aminoalkylbenzoate such as procaine, cocaine, an amino carbamate such as diperodon, a N-phenylamidine such as phenacine, a N-aminoalkyl amide such as dibucaine, an aminoketone such as falicain, or an aminoether such as pramoxine.

U.S. Pat. No. 6,030,974 describes a method of producing local anesthesia in a mammal experiencing pain in an epithelial tissue region. The method includes topically administering to the region, in a suitable pharmaceutical vehicle, an effective dose of a long-acting sodium channel blocking compound. The sodium channel blocking compound of U.S. Pat. No. 6,030,974 can be a formulation of tetrodotoxin or saxitoxin at a concentration of between 0.00–10 mM.

Omana-Zapata et al., Pain 72:41–49 (1997) discusses the utilization of tetrodotoxin for the inhibition of neuropathic ectopic activity in neuromas, dorsal root ganglia and dorsal horn neurons. The neuronal activity arises from neuroma caused by mechanical, chemical or ischemic injury. The effect of intravenously administered TTX on the neuronal induction by sciatic nerves in male rats was researched. However, the dosages and effects studied by Omana-Zapata et al. were applied to animals under anesthesia and artificial ventilation, thus these doses are above the maximal tolerated dose and the administration was under conditions that are not applicable to the presently intended clinical use of tetrodotoxin.

Topical administration of any sodium channel blocking compound to the vicinity of the teeth is not described in any of the above instances.

SUMMARY OF THE INVENTION

The methods and compositions of the present invention solve the long-recognized need in the art for methods of producing potent local anesthesia and analgesia of long duration. In the particular embodiment of producing long-lasting potent local anesthesia and analgesia on the tooth, the inventors have addressed a problem of great clinical significance, showing for the first time that sodium channel blocking compounds, such as tetrodotoxin and saxitoxin, can produce potent analgesic and anesthesia effects on pain induced by pulp stimulation of long duration and without evident side effects. Moreover, the inventors have shown that the effective doses of those sodium channel-blocking compounds have a wide margin of safety.

The methods and compositions of the invention can be used for any condition involving tooth pain, including local anesthesia following tooth surgery, and following injury to the tooth. The methods provide significant advantages, including providing at least 1 hour, preferably 2 hours and most preferably 6 hours of local anesthesia and analgesia, without evident side effects.

The present invention includes methods of producing potent long-lasting local anesthesia and analgesia, comprising administering a pharmaceutically acceptable composition of a long-acting sodium channel blocking compound, wherein the compound binds to the extracellular mouth of the sodium channel. In this manner sodium channel activity is inhibited by a mechanism distinct from that of local anesthetics, such as procaine, lidocaine and tetracaine. Preferably, such methods achieve potent local analgesia and anesthesia of long duration up to 6 hours. Preferred compounds include toxins or analogs thereof that specifically bind to a site formed in part by an extracellular region of the alpha subunit of a sodium channel. Most preferred compounds comprise the class of toxins and analogs that specifically bind to a site formed by the SS1 and SS2 extracellular regions of the alpha sub-unit of a sodium channel, wherein such compounds include tetrodotoxin, saxitoxin and analogs thereof. Surprisingly, these long-acting sodium channel blocking compounds, which are well known potent neurotoxins, provide potent long-lasting local analgesia and anesthesia without evident side-effects.

Accordingly, it is an object of the invention to provide a method of producing potent local analgesia and anesthesia in patients experiencing pain such as that associated with damage to tooth pulp, such as a decayed tooth, periodontitis and surgical procedures on a tooth.

In one aspect, the invention includes a method of producing potent local analgesia and anesthesia in a subject experiencing pain in the tooth pulp.

The invention lies partly in a method of producing local analgesia or anesthesia in nerve tissue of a mammal experiencing pain caused by damage to or stimulation of the nerve tissue. The method comprises administering to the nerve tissue of the mammal an anesthetically or analgesically effective dose of a pharmaceutical composition comprising a compound that binds to the SS1 or SS2 subunit of a sodium channel and a pharmaceutically suitable vehicle. The nerve tissue region can be a dental pulp region, a trigeminal nerve region, or a sciatic nerve region.

The method includes topically administering to the tooth pulp cavity, in a suitable pharmaceutical vehicle, an effective dose of tetrodotoxin or saxitoxin or analogs thereof.

In one embodiment, the effective dose of tetrodotoxin or saxitoxin is administered from a formulation containing tetrodotoxin or saxitoxin at a concentration of between 1 mM to 20 mM which causes a pain reducing effect for up to 6 hours.

In this application, tetrodotoxin is typically formulated in a vehicle having a pH of between 3.5 to 6.8.

In this application, the pharmaceutical composition does not produce toxic effects or any obvious deleterious side effects.

The present invention also includes a composition comprising a conventional local anesthetic compound that is a sodium channel blocking compound and a compound that binds to the SS1 or SS2 subunit of a sodium channel. The composition of the invention provides a synergistic effect of its component compounds to provide either or both of a more potent or a longer anesthetic effect.

BRIEF DESCRIPTION OF THE DRAWINGS

FIG. 1 shows a time-effect relationship of TTX after administration to the tooth pulp cavity.

FIG. 2 shows the synergistic effect of TTX when administered with tetracaine.

DETAILED DESCRIPTION OF THE INVENTION

As discussed above, the present invention provides a method of producing local analgesia and anesthesia in a subject experiencing pain in a sensory nerve region, typically tooth pulp, that is damaged or stimulated by chemical or physical cause, by administering a therapeutically effective dose of a sodium channel blocking compound, typically tetrodotoxin.

Tetrodotoxin is a nonprotein neurotoxin that is found in multiple diverse animal species, including puffer fish, goby fish, newt, frogs and the blue-ringed octopus.

Saxitoxin is a compound comprising a tetrahydropurine moiety composed of two guanidine units fused together in a stable azaketal linkage, having a molecular formula $C_{10}H_{17}N_7O_4$. Neosaxitoxin or hydroxysaxitoxin can be used as saxitoxins in the method of the invention.

In the examples described herein, tetrodotoxin was administered topically to the tooth pulp cavity and found to provide potent long-acting pain relief with no signs of systemic or local toxicity. The method of the present invention is intended for use in providing local analgesia and anesthesia for pain associated with tooth pulp stimulation resulting from various dental diseases and dental surgery.

Tetrodotoxin useful in the method of the present invention can be obtained from puffer fish organs. A detailed description of production of tetrodotoxin and derivatives thereof is provided in the Chinese patent application no. 00124516.3, filed Sep. 18, 2000.

Tetrodotoxin and Saxitoxin Formulation and Dosages

For use in the tooth region, tetrodotoxin and/or saxitoxin is typically administered in an aqueous solution. Typically, the active ingredient tetrodotoxin or saxitoxin is formulated into purified water or a physiological saline solution as a major vehicle. However, it will be appreciated that the dental formulation can contain other components, including, but not restricted to, buffering means to maintain or adjust pH, such as acetate buffers, citrate buffers, phosphate buffers and borate buffers; Administration of tetrodotoxin has been well studied in a number of animal species, and the lethal oral dose in human has been estimated to be about 10–18 µg/kg. For a 70 kg person, the lethal dose would therefore be 0.7–1.26 mg.

In the experiments performed in support of the present invention, described above, a 20 µL aliquot of 1 mM, 1.25 mM, 2.5 mM, 5 mM or 10 mM tetrodotoxin was administered topically to rabbits' tooth pulp cavity. This corresponds to a dose of between 6.4–64 µg of tetrodotoxin. If tetrodotoxin is administered in 10 µl, the dose of tetrodotoxin will be in a range of 3.2–32 µg. These doses are well below the lethal oral human dose and give a sufficient safety margin to allow for any differences in systemic absorption between topical and oral administration.

It will be appreciated that the dosage and concentration of tetrodotoxin or saxitoxin administered is determined on an individual basis, with consideration given to such factors as age and body weight of the patient, as well as to the route of administration and the clinical analgesic and anesthetic requirements.

The sodium channel blocker, preferably tetrodotoxin or saxitoxin, is typically administered topically to the painful tooth region by application of a formulation having a tetrodotoxin or saxitoxin concentration of between about 1–10 mM. The actual dose of tetrodotoxin or saxitoxin administered will, of course, depend on the amount of formulation applied and the surface area over which it is applied.

From the foregoing, it can be appreciated how various features and objectives of the invention are met. The method of the invention provides an effective, long-lasting local analgesia and anesthesia by topical administration of a long-acting sodium channel blocking compound to a painful tooth region. The examples below illustrate, using a rabbit model, that a single dose of tetrodotoxin at a concentration between 1 mM to 10 mM achieves potent local analgesia and anesthesia. The extent and duration of the effects depend on the concentration of tetrodotoxin.

One of skill in the art will appreciate that any of the long-acting sodium channel blocking compounds can be used according to the methods and procedures described herein to determine pharmaceutically or dentally effective doses and other aspects of the invention.

Synergistic compositions of the invention comprise at least one compound that specifically binds to the SS1 or to the SS2 subunit of a sodium channel, together with at least one conventional local anesthetic. In such synergistic compositions, the compound that binds to the SS1 or SS2 subunit of a sodium channel is preferably saxitoxin or tetrodotoxin, more preferably tetrodotoxin. The conventional local anesthetic is a sodium channel blocking compound, preferably tetracaine. In the compositions of the invention, the compound that binds to the SS1 or SS2 subunit of a sodium channel is typically present in an amount of from 1 to 10 mM, more typically in an amount of from 1 to 3 mM. The conventional local anesthetic is typically present in an amount representing one-half to two times its effective concentration, usually in an amount of from 0.2 to 5 percent by weight of the composition. Depending upon the components chosen as the SS1 or SS2 binding ingredient and as the local anesthetic, the composition can be prepared by mixing the ingredients immediately before administration, or can be mixed and then stored for later administration. This choice will depend in part upon what pH provides good stability to each ingredient. Ingredients requiring widely disparate pH for long-term stability should be mixed just prior to administration.

EXAMPLES

The following examples illustrate the methods and compositions of the invention, but are in no way intended to limit the invention.

$$\text{Percentage change} = \frac{\text{threshold voltage after dosing} - \text{threshold voltage before}}{\text{threshold voltage before}} \% \times 100$$

Experimental Example 1

Effect of Topical Administration of Tetrodotoxin on Pain Induced by Tooth Pulp Stimulation 60 New Zealand white rabbits were randomly divided into six groups to be treated with acetate buffer (as solvent control) or TTX at 1 mM, 1.25 mM, 2.5 mM, 5 mM and 10 mM, respectively. The test drugs were given by one injection of 20 µL to the tooth pulp cavity. The pulp cavity was reached by drilling through the tooth. The pain-inducing threshold voltage were measured prior to administration of drugs and again at 10 minute, 30 minute, 1 hour, 2 hours, 4 hours, 6 hours and 8 hours after administration. The results were shown as mean percentage change in pain-inducing threshold voltage±standard deviation and tabulated in Table 1.

TABLE 1

Effect of TTX by topical administration on the pain induced in the dental pulp of rabbits Percentage change in pain-inducing threshold voltage

| Group | N | 5 min | 10 min | 20 min | 30 min | 40 min | 50 min | 60 min | 90 min | 120 min | 240 min | 360 min | 480 min |
|---|---|---|---|---|---|---|---|---|---|---|---|---|---|
| Control | | 1 ± 8 | −1 ± 5 | −5 ± 4 | −2 ± 7 | −5 ± 5 | −6 ± 7 | −7 ± 10 | −3 ± 6 | −3 ± 5 | −2 ± 4 | −3 ± 4 | −2 ± 3 |
| 1 mM tetrodotoxin | 10 | 14 ± 15 | 26 ± 10 | 25 ± 14 | 30 ± 21 | 25 ± 20 | 21 ± 23 | 17 ± 19 | 6 ± 10 | 3 ± 7 **** | | | |
| 1.25 mM tetrodotoxin | 10 | 46 ± 30 | 66 ± 46 | 72 ± 38 | 60 ± 39 | 61 ± 28 | 69 ± 26 | 68 ± 23 | 36 ± 20 | 25 ± 24 **** | | | |
| 2.5 mM tetrodotoxin | 10 | 36 ± 20 | 64 ± 32 | 85 ± 37 | 88 ± 31 | 91 ± 31 | 101 ± 48 | 99 ± 46 | 82 ± 52 | 49 ± 49 | 17 ± 20 **** | | |
| 5 mM tetrodotoxin | 10 | 69 ± 38 | 78 ± 35 | 96 ± 46 | 109 ± 38 | 122 ± 46 | 122 ± 39 | 109 ± 49 | 116 ± 45 | 82 ± 35 | 41 ± 29 | 17 ± 20 **** | |
| 10 mM tetrodotoxin | 10 | 70 ± 31 | 90 ± 20 | 119 ± 39 | 123 ± 27 | 151 ± 57 | 151 ± 40 | 163 ± 76 | 141 ± 65 | 133 ± 68 | 99 ± 72 | 80 ± 46 | 23 ± 19 **** |

Note:
N is the number of animals in each group.
****: $p < 0.0001$ compared to the control group.

Animals: New Zealand white rabbits, purchased from the Animal Center of Beijing University, Beijing, P.R.China.
Materials: Tetrodotoxin, pure substance, solvent: acetate buffer, provided by Nanning Maple Pharmaceutical Co., Ltd. (Nanning, Guangxi, P.R. China).
Apparatus: CSI60 high-speed tooth drill, Shanghai Dental Appliance Factory (Shanghai, P.R.China). SEN-7103 electro-stimulator, Nihon Kohden, Japan.
The tetrodotoxin solution was dissolved in acetate buffer (pH 4.0) and prepared before each experiment.
Method: The experiments were performed according to the method developed by Voges et al. The voltage that induced the rabbit to lick for the first time was defined as pain-inducing threshold voltage. The electro-stimulating voltage was started from 0 V and was increased progressively by 0.25 volt each time until the pain-inducing threshold voltage was determined. The analgesic and anesthetic effects were evaluated by percentage change of the threshold voltage before and after the drug administration.

The results indicated that the threshold voltages did not change markedly in the rabbits given acetate buffer solution. TTX at all the five concentrations considerably increased the pain threshold voltages, demonstrating a clear concentration-dependent relation. TTX at 1 mM produced a relatively weak effect (p<0.001, F=32.55), while TTX at 10 mM generated the strongest effect (p<0.0001, F=91.51). The other three groups all increased the threshold voltages significantly (p<0.0001, F values were 107.13, 75.31 and 102.44, respectively). The onset of the effect of TTX increasing the threshold voltage was 5 minutes after dosing, and a peak was reached 1 hour after dosing.

Assuming a 50% or more increase in the threshold voltage to be effective, the results showed that the analgesia effect of TTX at 10 mM lasted more than 6 hours; TTX at 5 mM, 4 hours; TTX at 2.5 mM, 2 hours; TTX at 1.25 mM, only 1 hour.

The potency of TTX increased markedly with the increasing concentration of TTX at 30, 60, 90 and 120 minutes after dosing, and TTX at 10 mM produced the most potent effect (p<0.0001). TTX at 1 mM manifested considerable effect at three time points except for 120 minutes after dosing (p<0.001, 0.01, 0.05, respectively). The results in Table 1 and FIG. 1 also suggested that the duration of effectiveness of TTX was concentration-dependent as well.

Experimental Example 2

Determination of the Median Effective Concentration ($EC_{50}$) of TTX

A 50% increase in the threshold voltage was considered to be a criterion of effective local analgesia. A simplified probit unit method was utilized for the study and determination of the $EC_{50}$ of TTX for dental local analgesia.

Thirty rabbits were divided into three groups consisting of 10 rabbits each, and dosed with TTX at 1 mM, 1.125 mM and 1.25 mM, respectively, by one injection of 20 µL to the tooth pulp cavity. The pain threshold voltages in the rabbits were measured before and at time points up to 2 hours after dosing, and the percentage changes were calculated. Effective analgesia would be considered achieved if TTX increased the threshold voltage by 50% or more at any time point. The positive response rates were calculated to be 30% for TTX at 1 mM, 80% for TTX at 1.125 mM, and 100% for TTX at 1.25 mM. The $EC_{50}$ value of TTX and 95% confidence interval based upon the simplified probit unit method was 1.04±0.03 mM.

Experimental Example 3

Comparison of the Local Analgesia Action of TTX and Three Conventional Clinical Anesthetics Three conventional clinical anesthetics, lidocaine, procaine and tetracaine, were selected to compare to TTX. The same animal model was used in this experiment. Rabbits were divided into 6 groups of 10 each, and dosed with acetate buffer (solvent control), TTX at 1 mM, TTX at 1.25 mM, 2% lidocaine chloride (equal to 74 mM) and 1% tetracaine (equal to 33 mM), respectively, by one injection of 20 µL to the tooth pulp cavity. The threshold voltage was measured prior to dosing and at 6 time points within 1 hour after dosing. The results are shown in Table 2.

The results in Table 2 indicated that 2% procaine, acting similarly to the solvent control, had no clear effect on the threshold voltage in rabbits (p>0.05, F=0.15). 2% lidocaine and 1% tetracaine acted similarly in that they markedly increased the threshold voltage, p<0.01, F=10.09 and p<0.001, F=23.43, respectively, compared to the solvent control. The effects of lidocaine and tetracaine approximated that of TTX at 1 mM (p>0.05, F=0.0007 and 0.077, respectively), but were weaker than that of TTX at 1.25 mM (p<0.01, F=13.6 and p<0.001, F=18.5, respectively).

TABLE 2

Comparison of the effects of TTX and three local anesthetics

| Group | N | Percentage change in pain-inducing threshold voltage | | | | | |
|---|---|---|---|---|---|---|---|
| | | 10 min | 20 min | 30 min | 40 min | 50 min | 60 min |
| Solvent control | 10 | −1 ± 5 | −5 ± 4 | −2 ± 7 | −5 ± 5 | −6 ± 7 | −7 ± 10 |
| 1 mM tetrodotoxin | 10 | 26 ± 10 | 25 ± 14 | 30 ± 21 | 25 ± 20 | 21 ± 23 | 17 ± 19 **** |
| 1.25 nM tetrodotoxin | 10 | 66 ± 46 | 72 ± 38 | 60 ± 39 | 61 ± 28 | 69 ± 26 | 68 ± 23 **** |
| 2% procaine | 12 | −2 ± 20 | −2 ± 20 | −4 ± 23 | −3 ± 22 | −2 ± 28 | −1 ± 26 ^^^^ |
| 2% lidocaine | 10 | 30 ± 29 | 28 ± 36 | 26 ± 30 | 20 ± 32 | 24 ± 32 | 17 ± 21 **^^ |
| 1% tetracaine | 10 | 27 ± 30 | 32 ± 38 | 29 ± 31 | 32 ± 22 | 22 ± 15 | 16 ± 18 **^^^ |

Note:
N: number of animals in one group
Compared to the solvent control group
**: p < 0.01
****: p < 0.0001
Compared to the TTX 1.25 mM group
^^: p < 0.01
^^^: p < 0.001
^^^^: p < 0.0001

The comparison between difference groups was based upon analysis of variance for multiple measurement.

Experimental Example 4

Toxicity of TTX by Topical Administration

Clinical Signs of TTX Toxicity by Topical Administration

No deaths or adverse clinical signs were found in the rabbits dosed with TTX at concentrations ranging from 1 mM to 20 mM during all experiments. Only 4 out of 10 rabbits given TTX at 10 mM manifested increased excretion in the respiratory tract.

Effect of TTX by Topical administration on rabbit's heart rate, respiratory rate and ECG Five rabbits were anesthetized with 3% sodium pentobarbital (30 mg/kg, iv), then immobilized and connected to an electrocardiograph. The heart rate, respiratory rate and ECG were recorded. Then the rabbits were given 20 µL TTX at 20 mM in one injection into pulp of a tooth. The same parameters were measured at 15, 30, 60, 120, 240 and 360 minutes after dosing. The results, shown in Table 3, indicated that an injection of 20 μL TTX at 20 mM did not significantly modify the heart rate or respiratory rate of rabbits within 6 hours (p>0.05). The ECG did not suggest any significant effect of TTX either (p>0.05).

Blood Biochemical Effects of Tetrodotoxin by Topical Administration

Eight rabbits were divided into two groups, one acute dosing group and one chronic dosing group. Each in the acute dosing group was anesthetized with 3% sodium pentobarbital (30 mg/kg, iv) and immobilized on an operating table. A 3 mL blood sample was taken from the heart, with 1 mL to be used for analysis of blood cell content and 2 mL for measurement of blood biochemical parameters. Subsequently, twenty μL of TTX 20 at mM was given by one injection into the dental pulp cavity and a blood sample (3 mL) was taken again from the heart 1 hour after dosing. For the chronic dosing group, after blood samples taken, the rabbits were given TTX at 20 mM by one injection of 20 μL per day into the tooth pulp cavity for four days. After the last administration, the rabbits were anesthetized again to take blood samples from the heart. All blood samples were examined using standard clinical blood analytic methods on the same day they were taken. The results are shown in Tables 4, 5 and 6.

The results indicated that TTX at 20 mM given once or over four consecutive days did not have any significant effect on the blood cellular or biochemical parameters of the rabbits.

TABLE 3

Effect of TTX by topical administration on the heart rate and respiratory rate of rabbits

| Group | N | Before dosing | | After dosing | | | | | | | | | | | |
|---|---|---|---|---|---|---|---|---|---|---|---|---|---|---|---|
| | | | | 15 min | | 30 min | | 60 min | | 120 min | | 240 min | | 360 min | |
| | | HR | RR | HR | RR | HR | RR | HR | RR | HR | RR | HR | RR | HR | RR |
| TTX | 5 | 336 ± 33 | 82 ± 15 | 330 ± 30 | 91 ± 10 | 324 ± 33 | 94 ± 12 | 312 ± 27 | 99 ± 5 | 318 ± 16 | 99 ± 11 | 312 ± 27 | 102 ± 2 | 318 ± 27 | 102 ± 6 |

Note:
N: number of animals
HR: Heart rate
RR: Respiratory rate

TABLE 4

Effect of TTX by topical administration on the hematological parameters of rabbits

| Group | N | WBC (×10³/μl) | RBC (×10³/μl) | HGB (g/dl) | HCT (%) | MCV (fl) | MCH (pg) | MCHC (g/dl) | PLT (×10³/μl) |
|---|---|---|---|---|---|---|---|---|---|
| Control | 5 | 6.4 ± 2.3 | 6.3 ± 2.1 | 12.5 ± 2.3 | 43.3 ± 14.8 | 68.4 ± 2.7 | 20.6 ± 3.0 | 30.2 ± 4.7 | 195 ± 112 |
| Acute dosing | 5 | 4.2 ± 1.2 | 5.6 ± 0.6 | 12.4 ± 1.0 | 38.5 ± 3.4 | 68.5 ± 2.8 | 22.2 ± 1.4 | 32.4 ± 1.3 | 141 ± 120 |
| Chronic dosing | 3 | 6.6 ± 2.4 | 5.0 ± 0.4 | 11.3 ± 0.6 | 33.6 ± 1.9 | 66.9 ± 2.1 | 22.5 ± 1.1 | 33.6 ± 0.6 | 159 ± 37 |

Note:
N: number of animals

TABLE 5

Effect of TTX by topical administration on the contents of $Na^+$, $K^+$, $Cl^-$, $Ca^{2+}$ and $CO_2$ in the serum of rabbits

| Group | N | $Na^+$ (mmol/L) | $K^+$ (mmol/L) | $Cl^-$ (mmol/L) | $Ca^{2+}$ (mmol/L) | $CO_2$ (mmol/L) |
|---|---|---|---|---|---|---|
| Control | 5 | 142.9 ± 1.4 | 3.9 ± 0.5 | 102.2 ± 0.7 | 3.22 ± 0.21 | 26.8 ± 2.8 |
| Acute dosing | 5 | 141.1 ± 1.1 | 3.8 ± 0.3 | 102.7 ± 1.8 | 3.26 ± 0.18 | 26.4 ± 1.2 |
| Chronic dosing | 3 | 141.7 ± 1.8 | 3.8 ± 0.1 | 103.9 ± 2.5 | 3.34 ± 0.12 | 30.0 ± 2.5 |

Note:
N: number of animals

TABLE 6

Effect of TTX by topical administration on the hematological parameters of rabbits

| Group | N | ALT (U/L) | TBA (U/L) | ALP (U/L) | TP (g/L) | GTP (U/L) | LAP (µmol/L) | IP (mmol/L) | BUN (mmol/L) | Cre (µmol/L) |
|---|---|---|---|---|---|---|---|---|---|---|
| Control | 5 | 54 ± 22 | 18.2 ± 16.9 | 67 ± 23 | 60 ± 2 | 5.2 ± 1.1 | 106 ± 15 | 1.59 ± 0.10 | 8.5 ± 0.8 | 111 ± 14 |
| Acute dosing | 5 | 67 ± 43 | 13.5 ± 12.0 | 69 ± 17 | 60 ± 6 | 5.2 ± 1.3 | 109 ± 11 | 1.66 ± 0.23 | 8.4 ± 0.9 | 109 ± 12 |
| Chronic dosing | 3 | 53 ± 19 | 14.5 ± 9.2 | 71 ± 23 | 57 ± 6 | 5.7 ± 2.1 | 108 ± 10 | 1.46 ± 0.40 | 8.5 ± 1.7 | 99 ± 6 |

Note: N: number of animals

Experimental Example 5

Synergistic Activity of TTX and Another Local Anesthetic:

Rabbits were divided into 7 groups, and given TTX at 1 mM, 2% lidocaine, 1% tetracaine, TTX+lidocaine (TTM at 1 mM was given first and lidocaine 10 minutes later), lidocaine+TTX (2% lidocaine was given first and TTX at 1 mM 10 minutes later), TTX+tetracaine (TTX at 1 mM first and 1% tetracaine 10 minutes later) and tetracaine+TTX (1% tetracaine first and TTX at 10 minutes later), by an injection into the tooth pulp cavity of 20 µL. The threshold voltage was measured before dosing and at different time points after dosing. The percentage change of threshold voltage was calculated. The results are shown in Table 7 and FIG. 2.

The results in Table 7 showed that tetracaine+TTX produced a considerably stronger effect than TTX at 1 mM alone ($p<0.001$, F=23.85) or 1% tetracaine alone ($p<0.001$, F=23.5). The result was even stronger than the sum of the latter two. Lidocaine did not show a similar synergistic activity with TTX. The effect of tetracaine+TTX lasted 90 minutes, the longest duration of all groups.

To determine whether the positive synergistic action of TTX and tetracaine is observed when administered together, the following experiment is performed:

The test material and animal models are the same as above.

Determine the threshold voltages of tetracaine at concentrations of 1%, 0.1%, and 0.01% by the rabbit dental pulp stimulation model. The effect of tetracaine is considered positive if the threshold voltage increases by 30%. The minimum concentration of tetracaine that produces such an increase in the threshold voltage is defined to be the effective concentration, Ce. Separately determine the effect on threshold voltage of administering 10 µL of 1 mM TTX and the duration of the effect.

Mix 10 µL 1 mM TTX with 10 µL tetracaine at a concentration of 2× Ce and administer it promptly in one injection to the rabbit dental pulp and observe the effect of the formulation on the threshold voltage and the duration of the increase in threshold voltage. An observation of increase in threshold voltage or duration of anesthesia, or both, over the additive effects of tetracaine at Ce and TTX at 10 mM alone is indicative of a synergistic effect.

All publications and patent applications mentioned in this specification are herein incorporated by reference in their entirety and for all purposes by citation herein.

TABLE 7

Effect on the pain-inducing threshold voltage of rabbits by combination of TTX and a local anesthetic

| | | Percentage change in pain-inducing threshold voltage | | | | | | | |
|---|---|---|---|---|---|---|---|---|---|
| Group | N | 15 min | 30 min | 45 min | 60 min | 90 min | 120 min | 150 min | 180 min |
| 1 mM tetrodotoxin | 10 | 26 ± 10 | 30 ± 21 | 25 ± 20 | 17 ± 19 | 6 ± 10 | 3 ± 7 | | |
| 2% lidocaine | 10 | 30 ± 29 | 26 ± 30 | 20 ± 32 | 17 ± 21 | | | | |
| 1% tetracaine | 10 | 27 ± 30 | 29 ± 31 | 32 ± 22 | 16 ± 18 | | | | |
| tetrodotoxin + lidocaine | 8 | 36 ± 29 | 33 ± 35 | 35 ± 37 | 28 ± 36 | 16 ± 26 | 15 ± 21 | | |
| lidocaine + tetrodotoxin | 8 | 13 ± 14 | 21 ± 23 | 15 ± 27 | 14 ± 25 | 6 ± 21 | 5 ± 16 | | |
| tetracaine + tetrodotoxin | 10 | 73 ± 22 | 88 ± 33 | 80 ± 37 | 62 ± 39 | 44 ± 31 | 24 ± 33 | 16 ± 24 | 7 ± 18 ** ^^^ □□ |
| tetrodotoxin + tetracaine | 9 | 51 ± 30 | 30 ± 35 | 29 ± 36 | 17 ± 28 | 7 ± 26 | 8 ± 20 | 4 ± 15 | −4 ± 6 |

Note:
N: number of animals
Compared to the solvent control group:
**: $p < 0.01$
****: $p < 0.0001$
Compared to the TTX 1.25 mM group:
^^: $p < 0.01$
^^^: $p < 0.001$
^^^^: $p < 0.0001$
Compared to the TTX + tetracaine group:
□□: $p < 0.01$
The comparison between difference groups was based upon analysis of variance for multiple measurement.

Although the invention has been described with respect to particular embodiments, it will be apparent to one of ordinary skill in the art that many changes and modifications can be made thereto without departing from the spirit or scope of the invention.

REFERENCES

1. Du, P. and Yan, Y. J., Effect and Pharmacological Action of Tetrodotoxin on Sodium Channel, China Marine Drugs, 1–2:49–50 (1988)
2. Schwartz D. M. et al. Tetrodotoxin: Anesthetic Activity in the De-epithelialized Cornea. Graefes Arch Clin Exp Ophthalmol, 236(10): 790–4 (1998)
3. Schwartz, D. M. et al., Experimental Use of Tetrodotoxin for Corneal Pain After Excimer Laser Keratectomy, Cornea 17(2): 196–199 (1998).
4. Vogel, H. G. and Vogel W. H., Drug discovery and evaluation—pharmacological assays, Springer, Berlin, 374–75 (1997)
5. Xu, J. G., Molecular Biology of Foreign Medical Science, 26:1655 (1987)
6. Liu, Z. C. and Yu, S. Y (Editors-in-Chief), Nutrition and Food Hygiene, $2^{nd}$ edition, People's Hygiene Publishing Services, Beijing (1984).
7. Chen, Y. C. and Yuan, S. L., Research and Utilization of Toxins, Compilation of Theses of China Biochemistry Society Seminars, Vol. 4, Sciences Publishing Services, Beijing (1988).

We claim:

1. A method of producing local analgesia or anesthesia in nerve tissue of a mammal experiencing pain, comprising:

administering to dental pulp or a trigeminal nerve region of the mammal a first injection of a composition comprising a local anesthetic; and administering a second injection of a composition comprising a compound that binds to an SS1 or SS2 subunit of a sodium channel.

2. The method of claim 1, wherein a time gap between the first and second injections is up to about 10 minutes.

3. The method of claim 1, wherein the local anesthetic is tetracaine.

4. The method of claim 1, wherein the compound that binds to the SS1 or SS2 subunit of the sodium channel is tetrodotoxin.

5. The method of claim 1, wherein the local anesthetic is tetracaine and is present at a concentration of from 0.2% to 5%.

6. The method of claim 1, wherein local anesthetic is present at a concentration of from 0.1% to 5%.

7. The method of claim 1, wherein the compound that binds to the SS1 or SS2 subunit of the sodium channel is saxitoxin.

8. The method of claim 7, wherein the saxitoxin is administered in a concentration ranging from 1 mM to 20 mM.

9. The method of claim 7, wherein the saxitoxin is a compound comprising a tetrahydropurine moiety composed of two guanidine units fused together in a stable azaketal linkage, having a molecular formula $C_{10}H_{17}N_7O_4$.

10. The method of claim 7, wherein the saxitoxin is hydroxysaxitoxin or neosaxitoxin.

* * * * *